United States Patent
Zhou

(10) Patent No.: US 8,810,260 B1
(45) Date of Patent: Aug. 19, 2014

(54) DEVICE AND METHOD FOR DETECTING CHARACTERISTICS OF A MATERIAL OCCUPYING A VOLUME WITH CAPACTIVE SENSING OF MIRRORED PLATES

(75) Inventor: Yonghong Zhou, Beijing (CN)

(73) Assignee: Cypress Semiconductor Corporation, San Jose, CA (US)

( * ) Notice: Subject to any disclaimer, the term of this patent is extended or adjusted under 35 U.S.C. 154(b) by 1206 days.

(21) Appl. No.: 11/807,687

(22) Filed: May 29, 2007

Related U.S. Application Data

(60) Provisional application No. 60/909,593, filed on Apr. 2, 2007, provisional application No. 60/923,283, filed on Apr. 12, 2007.

(51) Int. Cl.
*G01R 27/26* (2006.01)

(52) U.S. Cl.
USPC ........................................ 324/658; 73/304 C

(58) Field of Classification Search
USPC .......................................................... 324/658
See application file for complete search history.

(56) References Cited

U.S. PATENT DOCUMENTS

| | | | |
|---|---|---|---|
| 3,934,475 A | 1/1976 | Rodgers et al. | 73/304 C |
| 3,935,739 A | 2/1976 | Ells | 73/304 C |
| 3,939,360 A | 2/1976 | Jackson | 307/118 |
| 3,986,110 A | 10/1976 | Overall et al. | 324/61 R |
| 3,991,614 A | 11/1976 | Ditzler | 73/215 |
| 4,099,167 A * | 7/1978 | Pomerantz et al. | 340/620 |
| 4,113,378 A | 9/1978 | Wirtz | |
| 4,194,395 A | 3/1980 | Wood | 73/304 C |
| 4,201,085 A | 5/1980 | Larson | 73/304 C |
| 4,209,740 A | 6/1980 | Marthe et al. | 324/61 R |
| 4,444,051 A | 4/1984 | Yamaki et al. | 73/304 C |
| 4,551,785 A * | 11/1985 | Kroner | 361/284 |
| 4,603,581 A | 8/1986 | Yamanoue et al. | 73/304 C |
| 4,749,988 A | 6/1988 | Berman et al. | 340/618 |
| 4,982,606 A | 1/1991 | Adamski et al. | 73/304 |
| RE34,073 E | 9/1992 | Suzuki | 324/687 |
| 5,182,545 A | 1/1993 | Goekler et al. | 340/620 |
| 5,207,098 A | 5/1993 | Koch et al. | 73/290 R |
| 5,739,598 A * | 4/1998 | Zatler et al. | 307/652 |
| 6,178,818 B1 | 1/2001 | Plöchinger | |
| 6,184,871 B1 | 2/2001 | Terés et al. | |
| 6,525,546 B1 * | 2/2003 | Zhao et al. | 324/658 |
| 6,542,350 B1 | 4/2003 | Rogers | 361/284 |

(Continued)

FOREIGN PATENT DOCUMENTS

GB  2358789 * 8/2001 ............ A47J 27/21

OTHER PUBLICATIONS

Tsui, Ted, "Migrating From CSR to CSD," Cypress Semiconductor Corporation—Application Note AN2408, Feb. 8, 2007, found at http://www.cypress.com.

*Primary Examiner* — Benjamin M Baldridge

(57) ABSTRACT

A system for sensing characteristics of a volume can include a mirror input configured to connect to a first mirror plate. The first mirror plate can be physically isolated from a first monitored space for containing a material. A sense input can be configured to connect to a first sense plate. The first sense plate can be positioned between the first mirror plate and the first monitored space, and can have a surface that faces the first monitored space. A capacitance sense section can generate a first sense value based on a capacitance at the sense input, and a mirror value based on a capacitance at the mirror input.

31 Claims, 10 Drawing Sheets

(56) References Cited

U.S. PATENT DOCUMENTS

| | | |
|---|---|---|
| 6,844,743 B2 | 1/2005 | Lenormand et al. ........... 324/663 |
| 6,918,296 B1 | 7/2005 | Urquidi et al. ............... 73/304 R |
| 6,923,056 B2 | 8/2005 | Urquidi ....................... 73/304 C |
| 6,988,405 B2 | 1/2006 | Jakoby et al. ................ 73/304 C |
| 7,017,409 B2 | 3/2006 | Zielinski et al. ............ 73/304 C |
| 7,038,467 B2 | 5/2006 | Urquidi ......................... 324/635 |
| 7,100,441 B2 | 9/2006 | Williams et al. ............ 73/304 C |
| 7,127,943 B1 | 10/2006 | Griffiths et al. ............. 73/304 C |
| 7,148,704 B2 | 12/2006 | Philipp |
| 7,161,361 B2 | 1/2007 | Qu et al. ........................ 324/690 |
| 2008/0088595 A1* | 4/2008 | Liu et al. ....................... 345/173 |
| 2008/0148877 A1* | 6/2008 | Sim .............................. 73/866.1 |

* cited by examiner

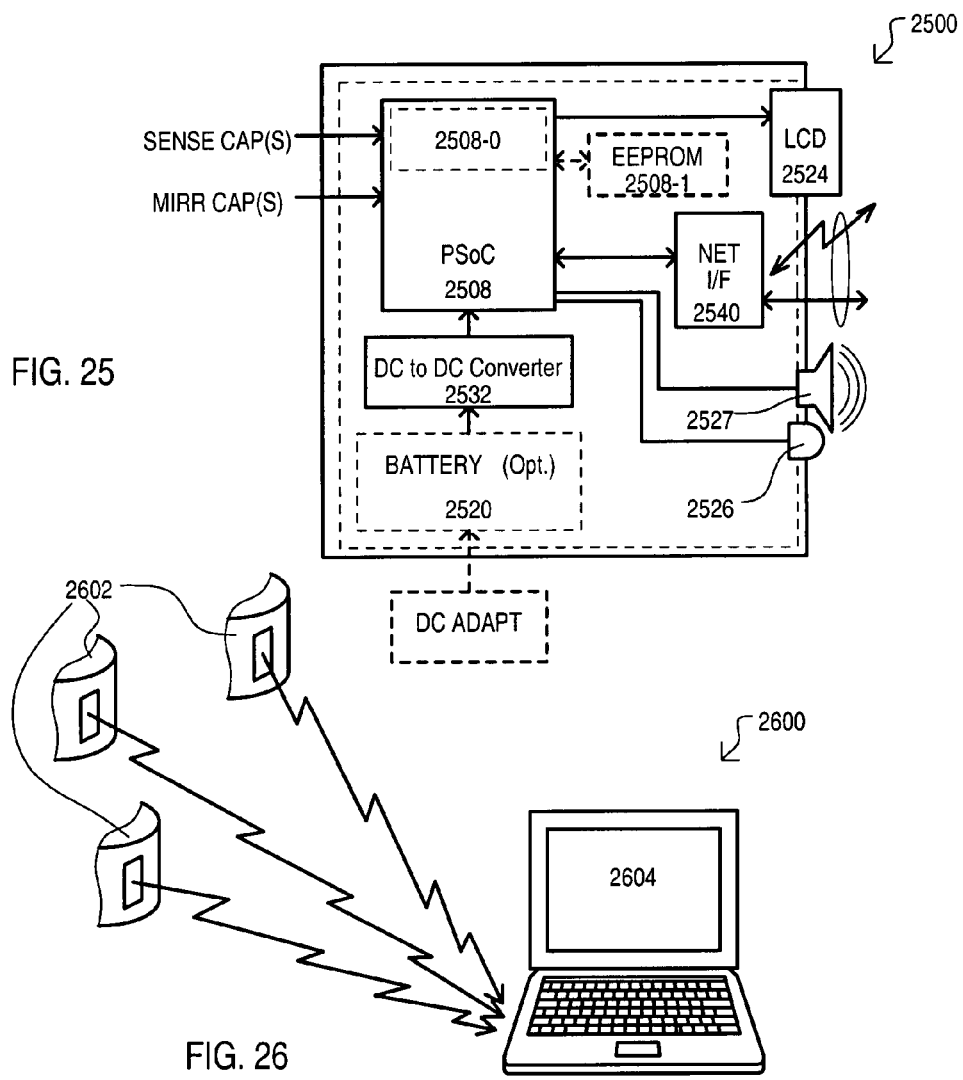
FIG. 25
FIG. 26
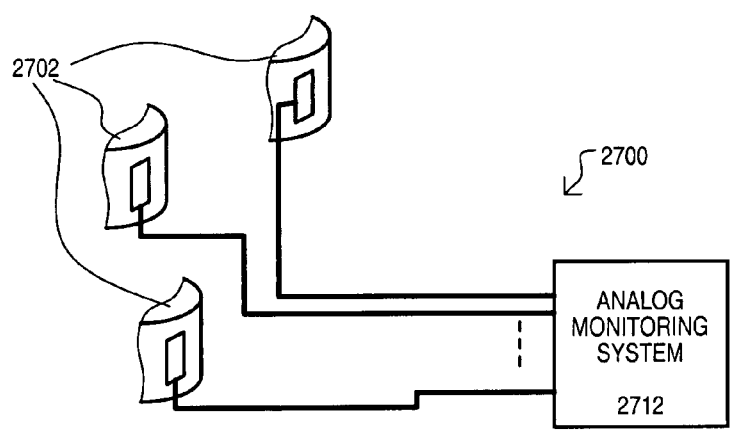
FIG. 27

DEVICE AND METHOD FOR DETECTING CHARACTERISTICS OF A MATERIAL OCCUPYING A VOLUME WITH CAPACTIVE SENSING OF MIRRORED PLATES

This application claims the benefit of U.S. provisional patent application Ser. No. 60/923,283 filed on Apr. 12, 2007, the contents of which are incorporated by reference herein, and the benefit of U.S. provisional patent application Ser. No. 60/909,593 filed on Apr. 2, 2007, the contents of which are incorporated by reference herein.

TECHNICAL FIELD

The present invention relates generally to measuring characteristics of materials within a container, and more particularly to measuring such characteristics with capacitive sensing.

BACKGROUND OF THE INVENTION

In many devices and manufacturing processes it can desirable to sense the characteristics of a material present in a container, or other type enclosure. For example, it may be desirable to detect the amount of space occupied by a material, such as the level of liquid within a container.

Conventional approaches to determining liquid levels have included mechanical devices. For example, floats have been employed that can actuate a switch to signal when a particular level has been reached. A drawback to such mechanical approaches can be limited reliability. Mechanical connections may freeze or otherwise malfunction for a variety of reasons, such as corrosion, lack of lubrication and wear. Further, to ensure proper operations mechanical switches can require ongoing maintenance, which can add to the cost of ownership for such devices or systems.

Capacitance sensing systems are known that can sense a level of a liquid within a container. Such conventional approaches can include a plate positioned on an inside surface or outside surface of a container. A capacitance presented by the plate can increase as the container volume occupied by a liquid increases, and vice versa. However, such a conventional approach can suffer from accuracy, as a sensed capacitance value can change according to environmental conditions, such as temperature. This can be a particular problem for sensing predetermined limits (i.e., almost empty or almost full), as such a limit value can change according to environment.

One very particular example of such a limit sensing difficulty can be with humidifier systems. Some conventional humidifier systems can include a reservoir having a heating element situated at the bottom. The reservoir can be filled with water and the heating element activated to evaporate the water. The heating element can be damaged, or its operating lifetime reduced if it is activated (is heating) while exposed to air. Thus, a water level sensor is needed in such to ensure the heating element is turned off while it is still submerged, or if no water is in the reservoir.

BRIEF DESCRIPTION OF THE DRAWINGS

FIGS. 12(a) and 12(b) showing examples of joining members for sense plates and mirror plates according to embodiments of the invention.

FIG. 23-28 are block diagrams showing various examples of capacitance sense systems according embodiments of the invention.

DETAILED DESCRIPTION

Various embodiments will now be described in detail that show methods and systems for detecting characteristics of a material utilizing one or more "sense" capacitor plates positioned to face the material, and one or more "mirror" capacitor plates. A sense capacitor plate can provide a capacitance value reflecting a characteristic of the material. A mirror capacitor plate can be situated in close proximity to the sense capacitor plate and provide a reference capacitance value that is essentially isolated from the material by the sense capacitor plate. A reference capacitance value can compensate for environmental changes that can cause variations in a sense capacitance value.

Figure 1:
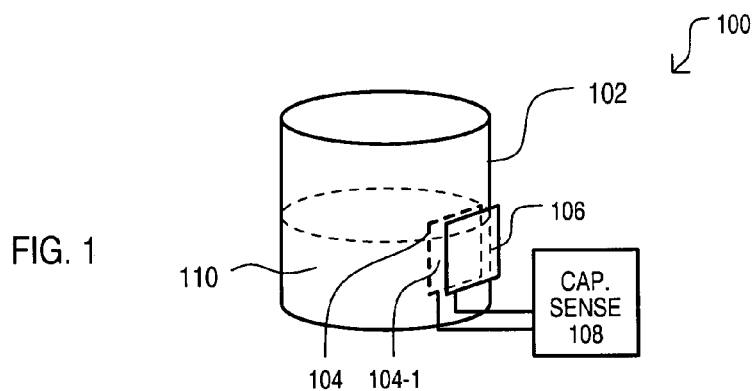
FIG. 1 is a block diagram showing a capacitance sense system according to a first embodiment.

Referring now to FIG. 1, a capacitance sense system according to first embodiment is shown in a block diagram and designated by the general reference character 100. A system 100 can include a container 102, a sense plate 104, a mirror plate 106, and a capacitance sense circuit 108. A container 102 can enclose, fully or partially, a space that can include a material 110.

A sense plate 104 can be formed from a conductive material and include a sense side (not shown in the view of FIG. 1) and an opposing non-sense side 104-1. A sense plate 104 can be positioned to have the sense side face container 102, and thus can present a capacitance that varies as a material 110 varies. For example, a capacitance sensed by sense plate 104 can vary as the amount of material varies. As another example, a capacitance sensed by sense plate 104 can vary as an inherent permittivity of the material 110 varies. A sense side of sense plate 104 can be directly exposed to the space enclosed by container 102 or indirectly exposed to such a space. In the first case, a sense side of sense plate 104 can be situated within container to make direct physical contact with material 110 (provided sufficient amount of the material is present in container 102). In the latter case, a sense side of sense plate 104 can make contact with an outside surface of container 104 and positioned to face the space enclosed by container 102.

A mirror plate 106 can be positioned to be exposed to the same general operating conditions as sensor plate 104, but not be exposed, either directly or indirectly, to the space enclosed by container 102. Thus, variations in operating conditions that can alter a capacitance sensed by sense plate 106 can affect the mirror plate 106 in the same fashion. Like sense plate 104, mirror plate 106 can be formed from a conductive material, and thus can present a capacitance. However, such a capacitance essentially does not vary as material 110 within the container varies. Preferably, a mirror plate 106 can be formed from the same material(s) as the sense plate 104. Even more preferably, mirror plate 106 can be formed from the same material(s) and have the same dimensions as the sense plate 104.

A sense plate 104 is preferably interposed between a mirror plate 106 and space that is monitored by the sense plate. In such an arrangement, a sense plate 104 can essentially block mirror plate 106 from being affected by changes in a material 110. When no material 110 is present in a container 102, sense plate 104 and mirror plate 106 can essentially form different plates of a same capacitor, and provide capacitance values that are nearly the same. However, when a material 110 is present within container 102, a capacitance of sense plate 104 can vary significantly from that of mirror plate 106.

A capacitance sense circuit 108 can have conductive connections to sense plate 104 and mirror plate 106, and can individually measure a capacitance presented by such plates. In particular, a capacitance sense circuit 108 can detect one or more characteristics of a material 110 by determining a capacitance of sense plate 104 and determining a capacitance of mirror plate 106. A capacitance of mirror plate 106 can be used to compensate for variations in capacitance presented by sense plate that arise due to changes in operating conditions.

It is noted that in an arrangement like that of FIG. 1, mirror plate 106 should be physically isolated to prevent any conductive bodies from getting in close proximity to the mirror plate. This can ensure that a mirror plate 106 capacitance accurately reflect changes due to the environment, and not those arising from such a close proximity conductive body. As but one example, a system 100 can be included in a housing with sufficient space around a mirror plate 106 to prevent significant variations in capacitance from arising due to local conductive bodies.

In this way, a capacitance sense system can include a mirror plate that can detect change resulting from the environment that can vary a capacitance value provided by a sense plate in close proximity.

Figure 2:
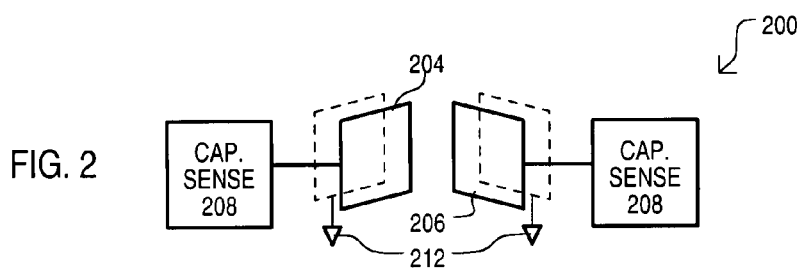
FIG. 2 is a representation of capacitance sense system according to an embodiment.

Referring now to FIG. 2, a representation of a system sensing operation according to an embodiment is shown in a block diagram, and designated by the general reference character 200. A system 200 shows some of the same general items as FIG. 1, thus like items are referred to by the same reference character but with the first digit being a "2" instead of a "1".

As shown in FIG. 2, in a system 200, a capacitance sense circuit 208 can sense a capacitance of a sense plate 204 (and hence sense a feature of a material) with respect to a reference potential 212, such as ground. In the same fashion, a capacitance sense circuit 208 can sense a capacitance of mirror plate 206 with respect to ground.

A sensing of each such plate (204 and 206) can vary according to application. For example, in cases where an operating environment is expected to change over time, a capacitance of mirror plate 206 can be measured each time that of sense plate 208 is measured. However, in other arrangements, where the environment is expected to change at a slower rate, a mirror plate 206 capacitance can be sensed less often, resulting in less power consumption for the system.

A capacitance sense circuit 208 can also vary according to application. For example, for more compact systems, a single capacitance measuring circuit can be included, and a capacitance for sense plate 204 and mirror plate 206 can be measured by multiplexing between the two. However, in other embodiments, separate capacitance measuring circuits can be provided for sense plate 204 and mirror plate 206.

In this way, a capacitance of a sense plate and mirror plate can be measured with respect to a common reference node (e.g., ground). Further, sampling rates and/or sampling circuits can vary according to application.

Figures 3A, 3B:
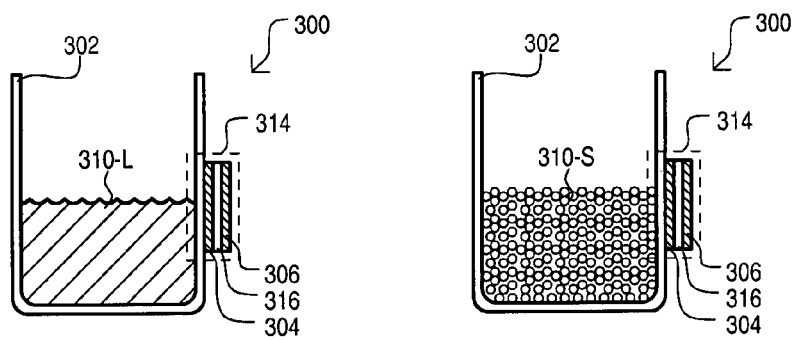
FIGS. 3A and 3B are side cross section views showing types of materials that can be sensed according to embodiments of the invention.

Referring now to FIGS. 3A and 3B, a few of the many possible examples of sensed materials are shown in diagrammatic form. FIGS. 3A and 3B show side cross sectional views of a system 300 including a container 302 and a sensor assembly 314. A sensor assembly 314 can include a sense plate 304, a mirror plate 306, and a joining member 316. A joining member 316 can enable mirror plate 306 to be situated adjacent to, and hence in the same operating environment as sense plate 304. A joining member 316 can be an insulating material, preferably with a relatively high degree of thermal conductivity to enable a mirror plate 306 temperature to follow that of the sense plate 304. In one very particular embodiment, sensor assembly 314 can include a circuit board with a sense plate 304 formed on one side and a mirror plate 306 formed on the opposite side.

It is understood that system 300 can further include a capacitance sense circuit (not shown), like that of FIG. 1 or any of the other embodiments and equivalents, that can separately measure a capacitance of a sense plate 304 and a mirror plate 306.

Each of FIGS. 3A and 3B show a container 302 that holds a material of different form. FIG. 3A shows an arrangement in which container 302 can hold a liquid material 310-L. As a level of liquid material 310-L changes, a capacitance at sense plate 304 can vary. More particularly, a capacitance of sense plate 304 can correspond to a level of liquid material 310-L within a container 302. A liquid can take various forms including, but not limited to, water, water based solutions, other inorganic liquids, as well as organic liquids, including petroleum based liquids.

Referring now to FIG. 3B, a system 300 is shown that includes a solid material 310-S. In level measuring applications, a solid material 310-S is preferably flowable (i.e., granular, particulate, etc.).

Of course, while the embodiments of FIGS. 3A and 3B show a sense plate 304 physically isolated from their respective material (310-L or 310-S), alternate arrangements can have a sense plate in physical contact with a material.

In this way, systems according to the embodiments can sense various types of materials.

While the above embodiments have shown systems with single sense plate/mirror plate pair, alternate embodiments can include multiple such pairs. A first example of such arrangement is shown In FIG. 4.

Figure 4:
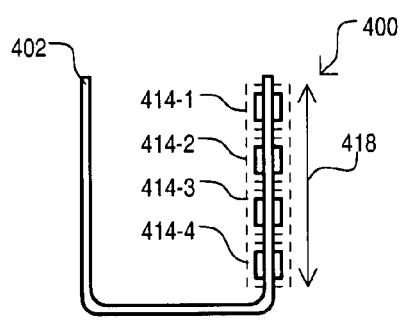
FIG. 4 is a side cross sectional view of a capacitance sense system according to an embodiment.

Referring now to FIG. 4, a system 400 can include a container 402 and multiple sensor assemblies 414-1 to 414-4. A container 402 can have a direction of movement, shown as 418 in FIG. 4. A direction of movement 418 can indicate the direction in which a material level is expected to vary as the amount of material is varied. For example, in one arrangement a direction of movement 418 can follow the direction of gravity. As more material is added to container 402, a material level can rise. However, in other arrangements, a direction of movement can be different. For example, for a container in a rotating system, a direction of movement 418 can follow the direction of the resulting centripetal force on the container.

It is understood that system 400 can further include a capacitance sense circuit (not shown), like that of FIG. 1, or other embodiments and equivalents, that can separately measure a capacitance of each sense plate and mirror plate in each sensor assembly (414-1 to 414-$n$).

In the particular embodiment of FIG. 4, sensor assemblies (414-1 to 414-$n$) can be spaced from one another along the direction of measurement. Each sensor assembly (414-1 to 414-$n$) can include a mirror plate and a corresponding sense plate situated between the mirror plate and the interior of container 402. Capacitance value for a sense plate and mirror plate in each different sensor assembly (414-1 to 414-$n$) can be measured. As a material level rises, a capacitance presented by each sense plate can vary.

An arrangement like that of FIG. 4 can provide for discrete level sensing, by determining when each sensor assembly (414-1 to 414-$n$) exceeds one or more limits. For example, if a capacitance of a sense plate increases when a material is next to a sensor assembly (414-1 to 414-$n$), a capacitance reading increase of the sense plate (with respect to its corresponding mirror plate) can indicate a material is at that level.

In addition to discrete level sensing, in arrangements where a material is expected to vary in a contiguous fashion along the direction of movement 418, an arrangement like that of FIG. 4 can provide for error detection. For example, if sensor assembly 414-1 indicates a material has reached its level, but sensor assembly 414-2 does not indicate so, an error indication can be generated.

As in the case of the various embodiments noted above, in sensor assemblies 414-1 to 414-$n$, a sense plate have a surface that doe not make physical contact with a material in the container 402 (e.g., is situated on an outer wall of the container), or can have a surface that makes physical contact with a material.

In this way, a system can include multiple sensor assemblies arranged in a detection.

While embodiments of the invention can include multiple sensor assemblies separated from one another in one direction, other embodiments can include different sensor assemblies arranged on two or more different sides of a container. Two possible examples of such an approach are shown in FIGS. 5($a$) to 5($d$).

Figure 5:
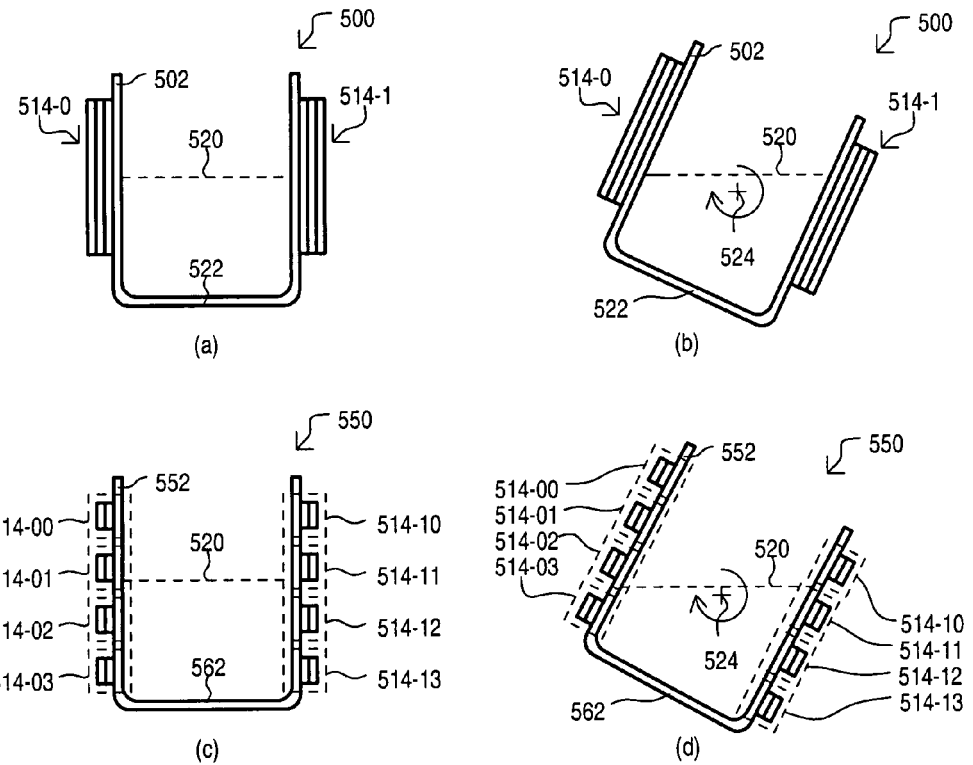
FIGS. 5(a) to 5(d) are side cross sectional views showing capacitance sense systems according to embodiments.

Referring now to FIGS. 5($a$) and 5($b$), a system is shown in a block diagram and designated by the general reference character 500. A system 500 can include a container 502 and two or more sensor assemblies 514-0 and 514-1. A container 502 can contain a material that can flow, and can vary in orientation with respect to gravity (or some other force acting on a contained material).

Sensor assemblies (514-0 and 514-1) can be situated on two or more different sides of a container 502. FIGS. 5($a$) and 5($b$) show an arrangement in which one sensor assembly (514-0) is situated on an opposing side of another (514-1). Each sensor assembly (514-0 and 514-1) can have a structure according to any of the embodiments described herein, and equivalents, including a mirror plate, and a sense plate interposed between the mirror plate and space enclosed by the container.

Like the embodiments of FIGS. 3A, 3B and 4, it is understood that system 500 can further include a capacitance sense circuit (not shown), like that of any of the embodiments shown herein or equivalents. Such a capacitance sense circuit can measure a capacitance of each sense plate and mirror plate in each sensor assembly (514-1 to 514-$n$).

Referring to FIG. 5($a$), container 502 is shown at a first orientation. In this orientation, a material level (shown by example as 520) will be at one position with respect to the sensor assemblies (514-0 and 514-1). In the very particular example of FIGS. 5($a$) and 5($b$), sensor assemblies (514-0 and 514-1) are aligned with one another with respect to a container bottom 522, thus a reading for both sensor assemblies (i.e., readings that take into account a capacitance of both a sense plate and a mirror plate) can be essentially the same. However, in other embodiments, sensor assemblies can have different orientations with respect to a container bottom, and thus provide different readings in such an orientation.

Referring to FIG. 5($b$), container 502 is shown in a second orientation that represents a rotation about an axis between sensor assemblies (514-0 and 514-1), which in FIG. 5($b$), is axis 524 going into the page. As a result, a material level 520 has a different position with respect to sensor assemblies (514-0 and 514-1). Thus, sensor readings for each sensor assembly (514-0 and 514-1) can change as compared to those corresponding to the orientation of FIG. 5($a$). For example, in the very particular arrangement shown, sensor assembly 514-1 can exhibit an increase in capacitance, while sensor assembly 514-0 can exhibit a decrease in capacitance. Such a change in capacitance values can be utilized to calculate an orientation of the container/material and/or an amount of material held by container 502.

Referring now to FIGS. 5($c$) and 5($d$), an alternate system is shown in a block diagram and designated by the general reference character 550. A system 550 can include the same general arrangement as that of FIGS. 5($a$) and 5($b$), but have multiple sensor assemblies, like those of FIG. 4, arranged along different sides of a container. In particular, sensor assemblies 554-00 to 554-03 can be arranged on one side of container 552, while sensor assemblies 554-10 to 554-13 can be arranged on another side of container 552.

In an arrangement like that of FIGS. 5($c$) and 5($d$), orientation and or general material amount can be determined by discrete level sensing of opposing of sensor assemblies on opposing sides of container 552.

System 550 can include a capacitance sense circuit (not shown) according to any of the embodiments or equivalents.

Referring to FIG. 5(c), container 552 is shown at a first orientation. In this orientation, a material level (shown by example as 520) can be detected by sensor assemblies 514-02, 514-03, 514-12 and 514-13, thus indicating one orientation. For example, such a level detection can occur in the same fashion as described with reference to FIG. 4. Of course, as in the case of FIGS. 5(a) and 5(b), sensor assemblies need not be aligned with one another with respect to a container bottom 522.

Referring to FIG. 5(d), container 552 is shown in a second orientation that represents a rotation about an axis 524 (going into the page). As a result, a material level 520 now has a different position. Now, a material level 520 can be detected by sensor assemblies 514-03, 514-11, 514-12 and 514-13, indicating a new orientation.

In this way, multiple sensors, each including a sense plate and mirror plate can be used to detect the orientation of a material with respect to a container.

Referring once again to FIGS. 5(a) and 5(c), multiple sensor sets like those of systems 500 and 550 can also be used for redundancy in applications where orientation of a container is not expected to change. That is, in the arrangement of FIG. 5(a), a sensor assembly 514-1 can provide a redundant reading with respect to sensor assembly 514-0. In the arrangement of FIG. 5(c), sensor assemblies 554-10 to 554-13 can provide redundant readings with respect to sensor assemblies 554-00 to 554-03, respectively. Thus, if readings between such sensors vary by a predetermined amount, an error indication may be generated. Similarly, if one sensor assembly is determined to have failed, the other can be used to continue operating the system. In such an arrangement, it may be desirable to have corresponding sensor assemblies on different container sides be aligned with one another with respect to a container bottom 522.

In this way, multiple sensors, each including a sense plate and mirror plate can be used to provide redundant readings for a material with respect to a container.

While the above embodiments have shown arrangements in which mirror plates are essentially shielded from detecting a material characteristic by a corresponding sense plate, alternate arrangements can include systems in which a mirror plate faces a different container space than that of a corresponding sense plate. Two such examples are shown in FIGS. 6 and 7.

Figure 6:
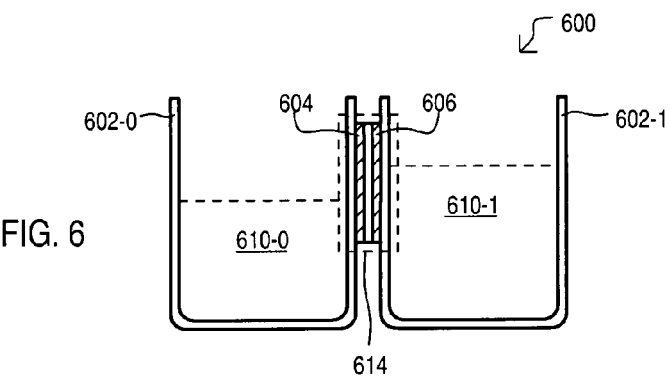
FIG. 6 is a side cross sectional view showing a capacitance sense system according to another embodiment of the invention.
Figure 7:
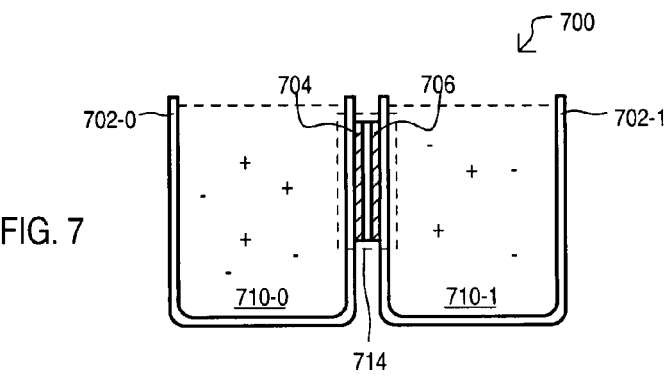
FIG. 7 is a side cross sectional view showing a capacitance sense system according to yet another embodiment of the invention.

Referring now to FIG. 6, a system according to another embodiment is designated by the general reference character 600 and shows a first container 602-0, a second container 602-1, and a sensor assembly 614. A first container 602-0 can enclose, fully or partially, a space that includes material 610-0. Similarly, second container 602-1 can enclose, fully or partially, a space that includes material 610-1.

A sensor assembly 614 can include a sense plate 604 with a sense side that faces first container 602-0. In addition, and unlike the arrangements described previously, mirror plate 606 can have a mirror side that that faces second container 602-1.

A capacitance sense circuit (not shown) can also be included in a system 600 for acquiring separate capacitance readings with respect to mirror plate 606 and sense plate 604.

In one particular configuration, a system 600 can generate a relative comparison between a capacitance sensed by mirror plate 606 with respect to that sensed by a sense plate 604. That is, assuming both containers (602-0 and 602-1) hold a same type material, when capacitance values are in the same general range, material levels in the two different containers can be considered the same. However, when separate capacitance measurements for sense plate 604 and 606 indicate significantly different values, materials levels can be considered to vary from one another.

An arrangement like that of FIG. 6, may be utilized in applications where it is desirable to maintain separate containers at the same or different levels. When maintaining a same level, when capacitance values indicate different levels, more material can be added to the appropriate container until levels are equal. Conversely, when maintaining different levels, when capacitance values indicate levels that are close to one another, more material can be added to one until a sufficient difference in levels exists.

Referring now to FIG. 7, a system according to another embodiment is shown and designated by the general reference character 700. System 700 can include the same general configurations as that of FIG. 6. Accordingly, like items are referred to by the same reference character but with the first digit being a "7" instead of a "6".

System 700 can differ from that of FIG. 6 in that levels of materials 710-0 and 710-1 in different containers are not expected to significantly vary. However, such materials are assumed to vary sufficiently in conductivity/permittivity to generate different capacitance readings. Thus, system 700 can sense a permittivity/conductivity characteristic giving rise to a change in capacitance, rather than a change in material level and/or orientation.

In this way, a sense plate and mirror plate can face different containers and provide relative capacitance indications for plates facing such containers.

While the above embodiments have shown arrangements in which systems include a one-to-one relationship between sense plates and mirror plates, in other arrangements a sense plate can be shared. One such embodiment is shown in FIG. 8.

Figure 8:
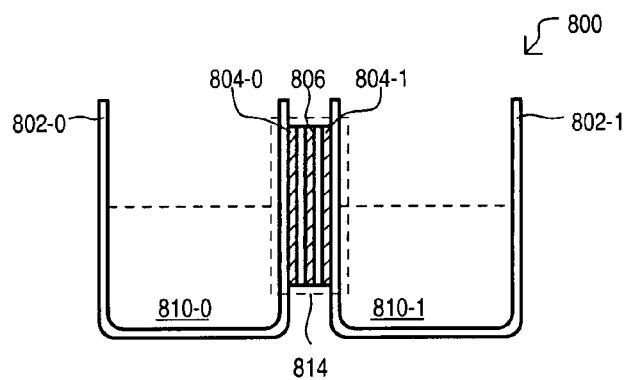
FIG. 8 is a side cross sectional view showing a capacitance sense system according to a further embodiment of the invention.

Referring now to FIG. 8, a system according to another embodiment is shown and designated by the general reference character 800. System 800 can include the same general configuration as that of FIG. 6.

However, unlike FIG. 6, a system 800 can include a sensor assembly 814 having a first sense plate 804-0, a second sense plate 804-1, and a shared mirror plate 806. A first sense plate 804-0 can sense capacitance variations arising from changes in a material 810-0 of a first container 802-0. Similarly, sense plate 804-1 can sense capacitance variations arising from changes in a material 810-1 of a second container 802-1. A capacitance of shared mirror plate 806 can be used to compensate for changes in environment that can affect readings taken by first and second sense plates (804-0 and 804-1).

In this way, a capacitance value taken from a mirror plate can be shared among multiple sense plates.

While the above embodiments have shown containers having particular shapes, the present invention should not necessarily be construed as being limited to such shapes and plate orientations.

Figure 9:
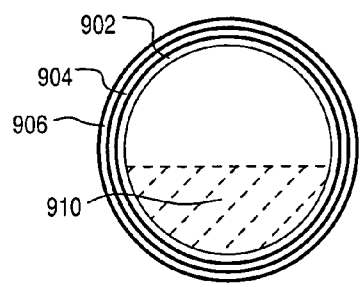
FIG. 9 is a side cross sectional view showing a capacitance sense system according to another embodiment of the invention.
Figure 10:
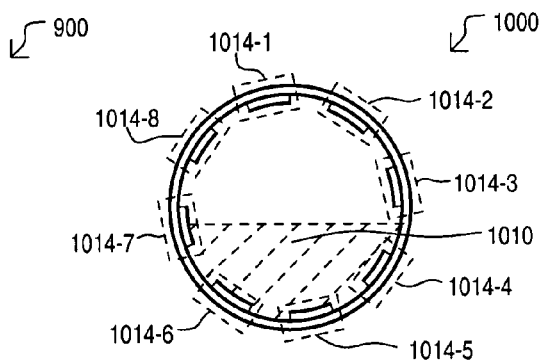
FIG. 10 is a side cross sectional view showing a capacitance sense system according to another embodiment of the invention.

As but one example of the many possible variations, capacitance sensing (and compensation using a mirror plate) can be implemented in containers having rounded walls, as shown in FIGS. 9 and 10.

FIG. 9 is a side cross sectional view showing a system 900 that can include a sense plate 904 and a mirror plate 906 formed on a container 902 Both sense plate 904 and mirror plate 906 can have annular shapes in cross section, with a sense plate 905 occupying an inner ring and mirror plate 906 occupying an outer ring. A system 900 can include a capacitance sense circuit (not shown) according to embodiments disclosed herein for separately reading a capacitance presented by each of sense plate 904 and mirror plate 906. It is understood that sense plate 904 and mirror plate 906 can be separated from one another by an insulating layer.

In the arrangement of FIG. 9, a capacitance value sensed by sense plate 904 can vary as a material 910 varies in amount, or other quality affecting permittivity. As in the other embodiments, a capacitance value sensed by mirror plate 906 can be used to compensate for environmental conditions that can result in variations of the values measured with sense plate 902.

Referring now to FIG. 10, a system 1000 according to yet another embodiment is shown in a side cross sectional view. System 1000 can have the same general configurations as FIG. 9, but can include a number of discrete sensor assemblies 1014-0 to 1014-8, each of which can include a sense plate and mirror plate.

In this way, one or more sense plates and mirror plates can be utilized to sense changes in capacitance for a containers of various shapes and configurations.

In the embodiments shown above, systems can include a sense plate having a surface that faces a container interior, with the sense plate being positioned between a mirror plate and a material or space being monitored by the sense plate. Such sense plate/mirror plate combinations can have a variety of orientations with respect to a container side. A few of the many possible examples of sensor plate/mirror plate configurations are shown in FIGS. 11(*a*) to 11(*f*).

Figure 11:
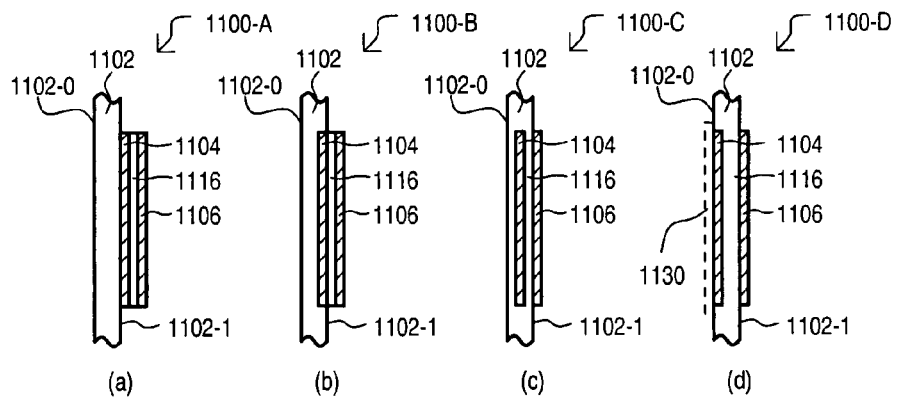
FIGS. 11(a) to 11(f) are side cross sectional views showing sense plate and mirror plate configurations according to various embodiments.
Figure 11:
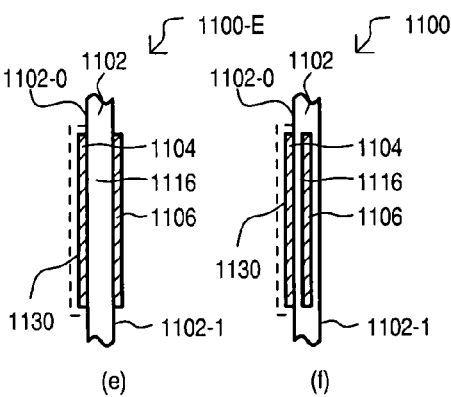

FIGS. 11(*a*) to 11(*h*) show examples of sensor assemblies 1100-A to 1100-F oriented with respect to a container 1102 having an outer surface 1102-0 and an inner surface 1102-1. Each sensor assembly (1100-A to 1100-F) can include a conductive sense plate 1104 and a conductive mirror plate 1106 separated from one another by a non-conductive joining member 1116.

Referring to FIG. 11(*a*), a sensor assembly 1100-A is shown that can be attached to an outside surface 1102-1 of container 1102. In such an arrangement, a sense plate 1104 can be attached to an outer surface 1102-1 by any suitable means, including but not limited to, adhesives or mechanical attachments. It is preferable that any mechanical attachment be done with insulating materials.

FIG. 11(*b*) shows an arrangement like that of FIG. 11(*a*), however a sense plate 1104 can be embedded into outer surface 1102-1.

FIG. 11(*c*) shows an arrangement like that of FIG. 11(*a*), however a sense plate 1104 can be situated between outer surface 1102-1 and inner surface 1102-1. In such an arrangement, if container 1102 is non-conductive, it can serve as a joining member 1116. A mirror plate 1106 can be situated on an outer surface 1102-1.

FIG. 11(*d*) shows an arrangement like that of FIG. 11(*c*), however a sense plate 1104 can be embedded into inner surface 1102-0. Optionally, a non-conductive protective coating 1130 can physically isolate a sense plate 1104 from a material being monitored.

FIG. 11(*e*) shows an arrangement like that of FIG. 11(*d*), however a sense plate 1104 can be situated on inner surface 1102-0. As in the case of FIG. 11(*d*), optionally, a non-conductive protective coating 1130 can physically isolate a sense plate 1104 from a material being monitored.

FIG. 11(*f*) shows an arrangement like that of FIG. 11(*e*), however a mirror plate 1106 can be situated between inner surface 1102-0 and outer surface 1102-1.

In this way, sense plates and mirror plates can have various orientations with respect to a corresponding container.

While embodiments above have shown arrangements in which a joining member can be co-extensive with opposing sides of a sense plate and mirror plate, this should not be construed as limiting to the invention. That is, a space between a sensor plate and mirror plate need not be filled with a material.

Figures 12, 13:
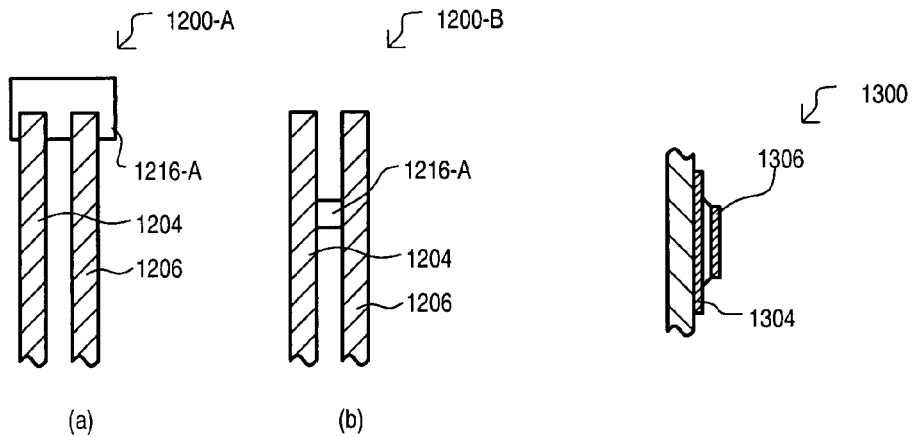
FIG. 13 is a side cross sectional view showing a scaled mirror plate arrangement according to an embodiment.

FIG. 12(*a*) shows arrangement in which a non-conductive joining member 1216-A can hold a sense plate 1204 in position with respect to a mirror plate 1206 at an end of such plates. A remaining space between sense plate 1204 and mirror plate 1206 can be a vacuum, an air gap, or some other non-conductive gas or liquid. FIG. 12(*b*) shows the same general arrangement as FIG. 12(*a*), but with a non-conductive joining member 1216-B being situated centrally with respect to sense plate 1204 and mirror plate 1206. One or multiple such joining members, can position sense plate 1204 and mirror plate 1206 to one another.

While a mirror plate can essentially match a sense plate in dimensions, in other embodiments a mirror plate can be scaled with respect to a sense plate. One such arrangement is shown in FIG. 13.

FIG. 13 shows a system 1300 having a mirror plate 1306 that is scaled in size with respect to a sense plate 1304. In such an arrangement, a capacitance value determined with mirror plate 1306 can be scaled with respect to that of sense plate 1304 in order to provide a compensating value. As but one very particular example, if a capacitance sensed by a mirror plate 1306 (Cmirror) is utilized to generate a limit condition (e.g., indicate when a material level is below or above a certain level), such a value can be scaled prior to being compared to a capacitance sensed by sense plate 1306 (K*Cmirror=Climit, where K varies according to relative size difference between sense plate and mirror plate).

In this way, a mirror plate can be a different size than a sense plate, but still be used to compensate for changes in environment that can affect readings taken with the sense plate.

While it may be desirable to consistently update a mirror plate capacitance value to account for changes in environment, in other applications such operations may be needed with less regularity. For example, a mirror plate may be utilized for infrequent calibration of values. In such an arrangement, a mirror plate can be removable. One such arrangement is shown in FIGS. 14(*a*) and 14(*b*).

Figures 14, 15:
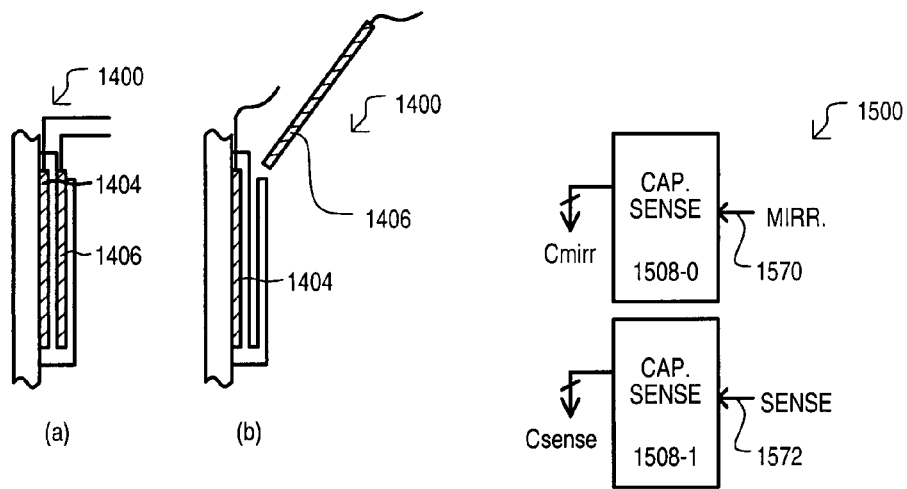
FIG. 14 is a side cross sectional view showing a removable mirror plate arrangement according to an embodiment.
FIG. 15 is a block diagram of a capacitance sense circuit according to an embodiment of the invention.

FIGS. 14(*a*) and 14(*b*) show a system 1400 like those described above, including a sense plate 1404 and a mirror plate 1406. However, a mirror plate 1406 can be removed. Of course, while FIGS. 14(*a*) and 14(*b*) show an arrangement having a slot 1450 to accept a mirror plate 1406, a removable mirror plate can be attached via other methods, such as non-conductive screws, clamps, temporary adhesives, etc.

In a system 1400, a removable mirror plate 1406 can be attached in proximity to a sense plate 1404. If needed, sufficient time can be allowed to pass to ensure that mirror plate 1406 can reflect current operating conditions. A capacitance of mirror plate 1406 can then be sensed one or more times, and such a value stored. This value can then be used to modify a capacitance measured with sense plate 1404.

In this way, a mirror plate can be removable.

Having described various arrangements in which sense plates and mirror plates can be arranged with respect to one another, various examples of possible sense circuits that can included in the embodiments will now be described.

Referring to FIG. 15, a capacitance sense circuit according to one embodiment is shown in a block schematic diagram and designated by the general reference character 1500. A capacitance sense circuit 1500 can include a first sense circuit 1508-0 and second sense circuit 1508-1. A first sense circuit 1508-0 can have a mirror input 1570 that can be connected to a mirror plate that can take the form of any of the embodiments described herein, or equivalents. First sense circuit 1508-0 can be capable of generating value Cmirr that corresponds to a capacitance measured via mirror input 1570.

In a similar configuration, a second sense circuit 1508-1 can have a sense input 1572 that can be connected to a sense plate according to any of the embodiments described herein, or equivalents. Second sense circuit 1508-1 can be capable of generating value Csense that corresponds to a capacitance measured via sense input 1572.

In this way, a capacitance of a mirror plate and sense plate can be measured by entirely different circuits.

Figure 18:
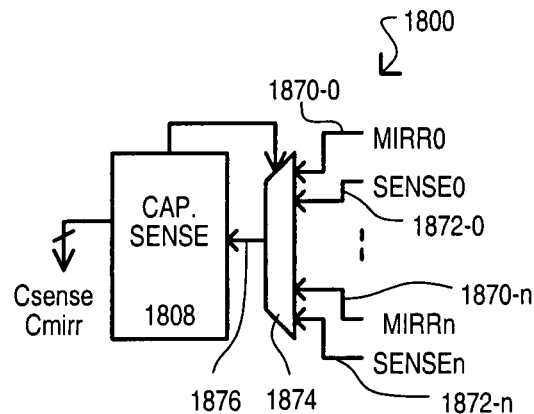
FIG. 18 is a block diagram of a capacitance sense circuit according to a further another embodiment of the invention.

While FIG. 15 shows measurement of mirror and sense capacitance values by separate sense circuits, preferably, such values can be measured by a common sense circuit. Various examples of such arrangements are shown in FIGS. 16 to 18.

Figures 16, 17:
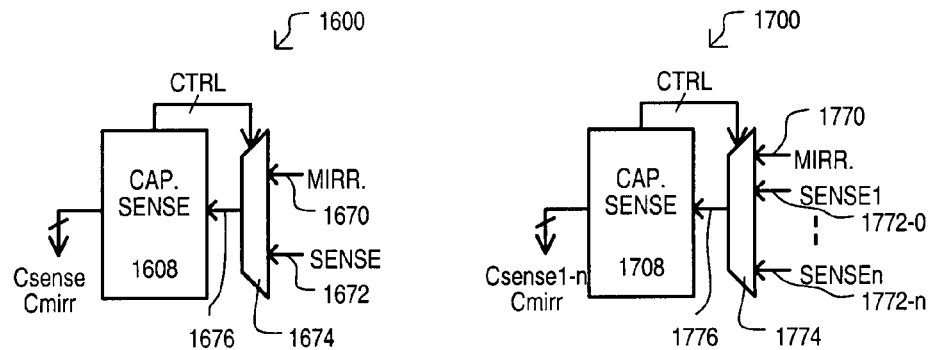
FIG. 16 is a block diagram of a capacitance sense circuit according to another embodiment of the invention.
FIG. 17 is a block diagram of a capacitance sense circuit according to yet another embodiment of the invention.

Referring to FIG. 16, a capacitance sense circuit 1600 can include a sense circuit 1608 and an input multiplexer (MUX) 1674. A sense circuit 1608 can generate a value representative to a capacitance presented at a sense input 1676.

An input MUX 1674 can include a mirror input 1670 and sense input 1672 that can be connected to a mirror plate and sense plate, respectively, according to any of the embodiments described herein, or equivalents. An output of input MUX 1674 can be connected to sense input 1676. Sense circuit 1608 can provide selection signal CTRL to MUX 1674 to allow separate connection to inputs 1670 and 1672 to sense input 1676. Thus, sense circuit 1608 can be capable of generating a value Cmirr that corresponds to a capacitance measured via mirror input 1670 as well as a value Csense that corresponds to a capacitance measured via sense input 1672.

In this way, one capacitance sense circuit can multiplex inputs to provide mirror and sense capacitance values.

Referring now to FIG. 17, a capacitance sense circuit according to another embodiment is shown in a block diagram and designated by the general reference character 1700. FIG. 17 has the same general arrangement as FIG. 16, thus similar structures are referred to bye the same reference characters but with the first digits being "17' instead of "16". FIG. 17 can differ from that of FIG. 16 in that MUX 1774 can have one mirror input 1770 that can be connected to a mirror plate, and multiple sense inputs 1772-0 to 1772-n.

Referring now to FIG. 18, a capacitance sense circuit according to yet another embodiment is shown in a block diagram and designated by the general reference character 1800. FIG. 18 has the same general arrangement as FIG. 16, thus similar structures are referred to bye the same reference characters but with the first digits being "18' instead of "16". FIG. 18 can differ from that of FIG. 16 in that MUX 1874 can have mirror/sense input pairs (1870/2-0 to 1870/2-n).

In this way, mirror and sense values can be generated by one or more sense circuits.

Figure 19:
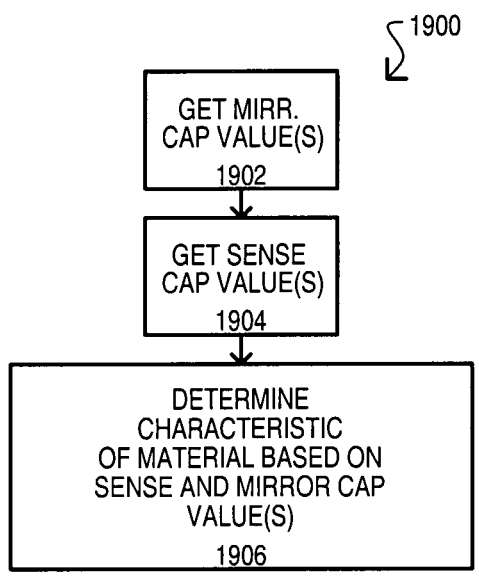
FIG. 19 is a flow diagram of a capacitance sense method according to an embodiment.

Referring now to FIG. 19, a method according to an embodiment is shown in a flow diagram, and designated by the general reference character 1900. A method 1900 can include measuring a capacitance value at one or more mirror plates (step 1902). Such step can include measuring a capacitance value seen by a mirror plate with respect to a reference potential, which can be ground. Even more particularly, a mirror plate can be electrically connected to a sense circuit that measures a capacitance according to relaxation oscillator techniques and/or delta-sigma modulation techniques. Such a circuit can generate a numerical value corresponding to the sensed capacitance.

A method 1900 can then measure a capacitance value at one or more sense plates (step 1904). Such step can include the same general actions as step 1902 but with respect to a sense plate rather than a mirror plate.

Thus, steps 1902 and 1904 can represent separate capacitance measurements independent of one another. That is, a capacitance between such plates is not measured, but rather, a capacitance of each plate with respect to a common reference is measured.

A method 1900 can further include determining a characteristic of a material based on sense and mirror capacitance values (step 1906). Such a step can include modifying one or more limit value according to the mirror capacitance, and comparing such a limit value to sense capacitance value. Alternatively, such a step can include modifying the sense capacitance value itself based upon the mirror capacitance. Of course, these are but two of many possible ways in which step 1906 can be executed.

In this way, a method can utilize a capacitance reading of a mirror plate exposed to the same environment as a sense plate, to generate a characteristic value for a material monitored by the sense plate.

Having described various systems and methods that can include capacitance sense circuits, particular examples of capacitance sense circuits that can be included in the various embodiments will now be described.

Figure 20:
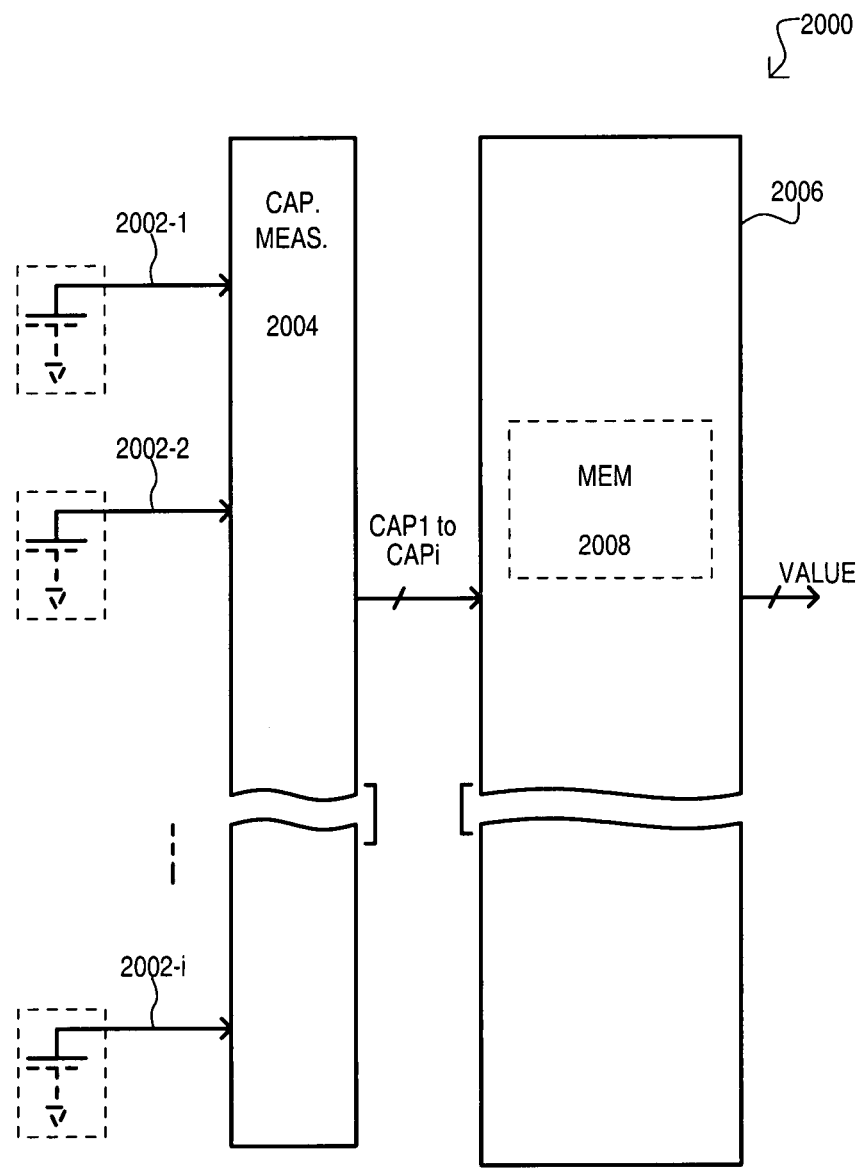
FIG. 20 is a blocks schematic diagram of a capacitance sense circuit according to an embodiment.

Referring now to FIG. 20, a capacitance sense circuit according to one embodiment is shown in a block schematic diagram and designated by the general reference character 2000. A capacitance sense circuit 2000 can have inputs 2002-1 to 2002-i connected to one or more plates, such as a sense plate or a mirror plate according to the embodiments described herein, or equivalents.

A capacitance sense circuit 2000 can include a capacitance sensing section 2004 and a computation section 2006. A sensing section 2004 can generate capacitance values CAP1 to CAPi corresponding to each input (2002-1 to 2002-i).

A sensing section 2004 preferably generates numerical values as capacitance values (CAP1 to CAPi), even more preferably, generates a sense count value based upon a charging of a sense plate and a mirror plate value based upon a charging of a mirror plate. A sensing section 2004 can include a sensing circuit for each input, but may preferably multiplex (MUX) inputs to a common sense node.

A sensing section 2004 can also include one or more charging sources (e.g., current sources). In particular, one charging source may be spread among inputs (2002-1 to 2002-i) in a multiplexed approach, or individual charging sources may be provided corresponding to each input (2002-1 to 2002-i). A charging source can take any of a number of possible forms. In one simple approach, a charging source can be a resistor that is connected directly, or by way of a switching arrangement, to an input (2002-1 to 2002-i). Alternate approaches can include current digital-to-analog converters (current DACs), or reference current sources biased according to well known temperature independent techniques (band-gap reference, etc.).

In very particular embodiments, a sensing section 2004 can utilizes modulation (e.g., sigma-delta modulation) to determine sense plate and/or mirror plate capacitance values. In such arrangements, a sensing section 2004 can include a switched capacitor network, with modulation capacitor and other elements being shared with capacitance sensors in a multiplexed approach.

A computation section 2006 can execute predetermined arithmetic and/or logic operations. A computation section 2006 can generate material characteristic values based on the capacitance of one or more sense plates and the capacitance of one or more corresponding mirror plates. A material characteristic value can be generated via a computation, or via look-up table, or the like. In one very particular arrangement, a computation section 2006 can include a memory 2008 for storing instructions executable by computation section 2006.

In this way, a capacitance sense circuit can generate numerical values for a capacitance of one or more sense plate(s) and at least one corresponding mirror plate, and compute or otherwise generate a material characteristic value based upon such numerical values.

Figure 21:
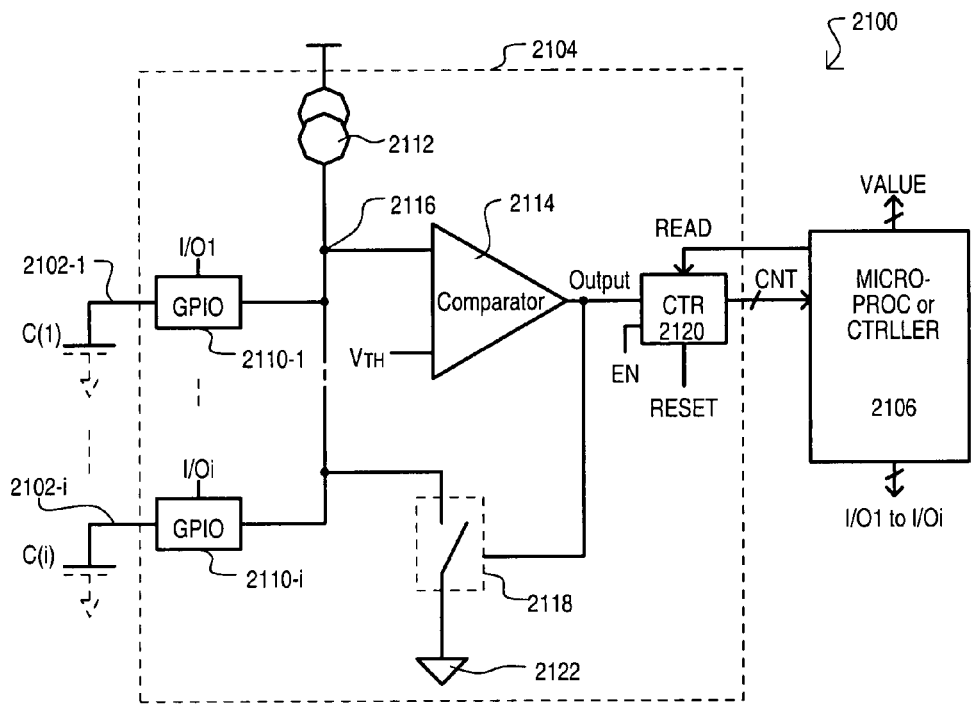
FIG. 21 is a block schematic diagram of a capacitance sense circuit according to an embodiment.

Referring now to FIG. 21, a capacitance sense circuit according to another embodiment is shown in a block schematic diagram and designated by the general reference character 2100. A capacitance sense circuit 2100 can be a relaxation oscillator type circuit that charges and discharges a sense plate or mirror plate to determine a capacitance value for such a plate. For example, a sense or mirror plate can be set at one potential, and allowed to discharge (or charge) to second potential. The number of times an oscillating signal transitions while the plate is between the two levels can be counted. As but another example, the number of times a sense plate or mirror plate can be charged and discharged by known current sources/sinks in a constant time period can be counted.

Referring still to FIG. 21, a capacitance sense circuit 2100 can include a sensing section 2104 and a calculation section 2106. A sensing section 2104 can include a number of input/output (IO) cells 2110-1 to 2110-*i*, a current source 2112, a comparator 2114, a reset switch 2118, and a counter 2120. Each input (2102-1 to 2102-*i*) can be connected to a corresponding IO cells (2110-1 to 2110-*i*). Individual IO cells (2110-1 to 2110-*i*) can be connected to a common bus 2116 in a multiplexer type fashion. IO cells (2110-1 to 2110-*i*) can each be controlled by corresponding I/O signals I/O1 to I/Oi.

Current source 2112 can be connected to common bus 2116 and provide a current thereto. Such a current can be constant current when making capacitance measurements. Preferably, current source 2112 can be programmable to accommodate variations in a sensed capacitance value. Reset switch 2118 can be connected between common bus 2116 and a low power supply node 2122. Reset switch 2118 can be controlled according to an output of comparator 2114.

Comparator 2114 can have one input connected to common bus 2116, a second input connected to a threshold voltage $V_{TH}$ and an output connected to reset switch 2118 and to counter 2120.

Counter 2120 can be a gated counter that can accumulate transitions at the output of comparator 2114. In particular, in response to an enable signal EN, counter 2120 can perform a counting operation. In response to a reset signal RESET, counter 2120 can reset a count value to some predetermined starting value (e.g., 0). In response to a read signal READ, counter 2120 can output an accumulated count value CNT. In one very particular arrangement, a counter 2120 can be a 16-bit timer with an externally triggered capture function.

In operation, compare section 2104 can multiplex capacitance readings by sequentially enabling (e.g., placing into a low impedance state) IO cells (2110-1 to 2110-*i*). While one IO cell is enabled, current source 2112 can charge the capacitance at the corresponding input (i.e., a selected mirror plate or sense plate). Once a potential at common bus 2116 exceeds voltage $V_{TH}$, an output of comparator 2112 can transition from an inactive to active state, turning on reset switch 2118, thus discharging common bus 2116. In this time period, a counter 2120 can generate a count value.

Alternatively, the charging process at common bus 2116 can be repeated to generate an oscillating signal at the output of comparator 2114. Such an oscillation rate can be counted by counter 2120 over a predetermined time period to generate a count value. Once a count value has been acquired from one input, the current IO cell can be disabled and a new IO cell enabled. The operation can then be repeated to generate count values for all plates of interest.

A calculation section 2106 can generate characteristic values based on readings generated by capacitance sensors (2102-1 to 2102-*i*). A calculation section 2106 can include a microprocessor core or microcontroller that receives count values from counter 2120, and executes arithmetic operations to generate characteristic values of a monitored material.

In this way, a sensing circuit can process capacitance values with a relaxation oscillator type circuit.

While relaxation oscillator circuits can be used to determine a capacitance of a sense plate or mirror plate, other embodiments can include different methods. One such example is shown in FIG. 22.

Figure 22:
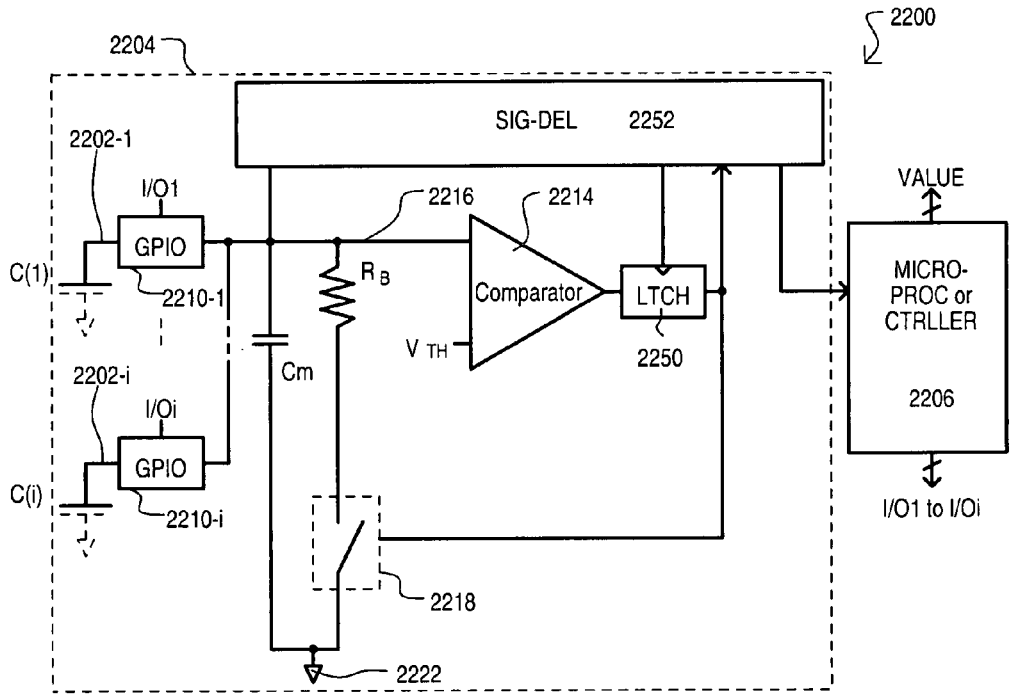
FIG. 22 is a block schematic diagram of a capacitance sense circuit according to an embodiment.

Referring now to FIG. 22, a capacitance sense circuit according to another embodiment is shown in a block schematic diagram and designated by the general reference character 2200. A capacitance sense circuit 2200 can be a delta-sigma type circuit that connects a plate (i.e., sense plate or mirror plate) to an input of a comparator. The comparator input can be set to an initial value. An output of the comparator can be periodically sampled. Once a comparator input exceeds (or falls below) a threshold voltage, the comparator output can switch, and the comparator input can be increased (or decreased) by a set amount, until it is once again below (or above) the reference voltage.

Referring still to FIG. 22, a capacitance sense circuit 2200 can include a sensing section 2204 and a calculation section 2206. In the very particular example of FIG. 22, a sensing section 2204 can include elements for forming an input switched capacitor network in conjunction with inputs (2202-1 to 2202-*i*). A modulation capacitor Cm can be connected in parallel with a "bleed" resistor $R_B$ to common bus 2216. Further, a reset switch 2218 can be connected between bleed resistor $R_B$ and a low power supply node 2222. Values output from comparator 2214 can be latched in output latch 2250. Output latch 2250, in turn, can control reset switch 2218.

Referring still to FIG. 22, a capacitance sense circuit 2204 can include a sigma-delta modulation control circuit 2252. Control circuit 2252 can generate timing control signals for controlling the operation of output latch 2250. Further, control circuit 2252 can include switching circuits for charging common bus 2216 during a sampling operation.

More detailed examples of sigma-delta modulation are shown in "Migrating from CSR to CSD", by Ted Tsui, an Application Note published by Cypress Semiconductor Corporation, the contents of this article are incorporated by reference herein.

Of course, while the embodiments of FIGS. 21 and 22 show a microprocessor or microcontroller core, this represents but one type of calculation section. Alternate embodiments could be realized by an application specific integrated circuit (ASIC) or programmable logic device, to name but a few examples.

Embodiments of the invention can also include systems that provide local indications or allow for remote sensing/detection. Various examples of such embodiments will now be described.

Figure 23:
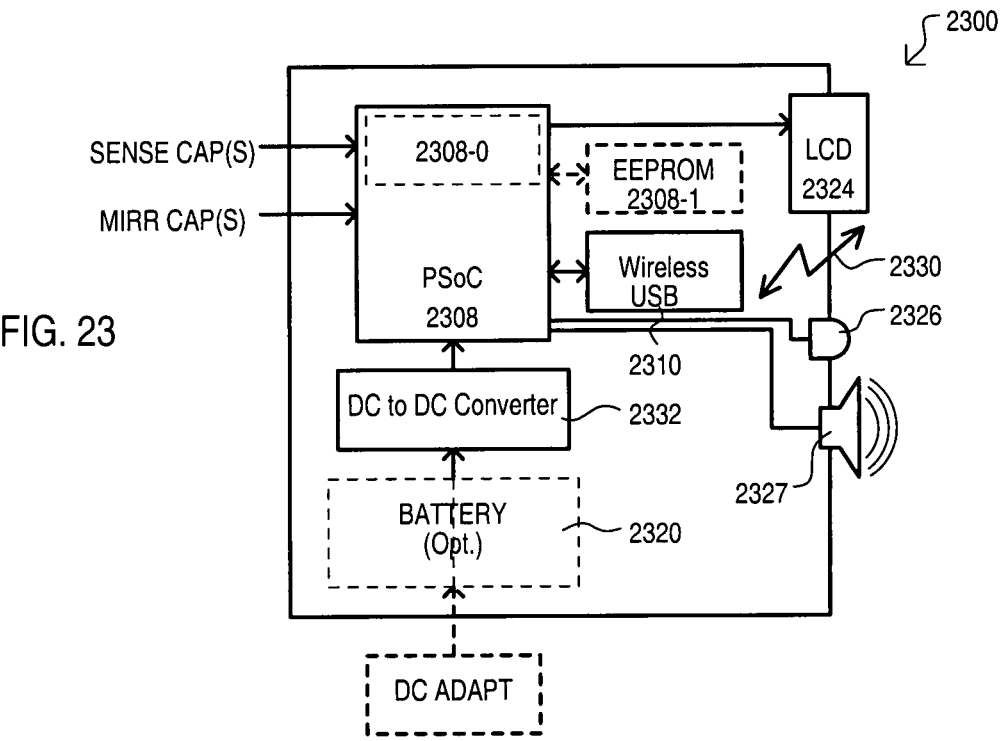

Referring now to FIG. 23, a capacitance sensing system 2300 can include a control IC section 2308, a battery receiver 2320 (optional), a DC to DC converter 2322, and transmitting circuit 2310. Control IC section 2308 can include capacitance sensing circuits and controller circuits for generate a material characteristic value. Such sensing circuits can include one or more integrated circuits and any necessary discrete components. Optionally, an on-board storage circuit 2308-0 can store instructions for execution by control IC section 2318. On-board storage circuit 2308-0 preferably includes nonvolatile storage circuits, such as a programmable read-only-memory (PROM), electrical PROM (EPROM), electrically erasable PROM (EEPROM, including "flash" EEPROM), magneto-resistive random-access memory (MRAM), ferroelectric RAM (FRAM), or phase change RAM. Such nonvolatile storage circuits can be used in combination with volatile storage circuits, such as dynamic RAM or static RAM. Preferably, a control IC section 2318 can be a PSoC™ Mixed-Signal Array manufactured by Cypress Semiconductor Corporation of San Jose, Calif., USA.

A control IC section 2308 can include additional functions. A control IC section 2308 can control the activation of all or any of the other circuits of system 2300. For example, circuits can be activated only when needed for a given function, and then returned to a deactivated state. A deactivated state can be a standby state or an off state, for example. Even more particularly, a control IC section 2308 can activate circuits periodically to generate and transmit characteristic values generated from sense and mirror plate capacitance values, and then deactivate such circuits. In addition or alternatively, a control IC section 2308 can activate such circuits when requested by a user input, and then return such circuits to a deactivated state. Such an approach can advantageously conserve power consumption, which can be particularly beneficial in battery powered embodiments.

In the event additional memory is needed beyond that available by circuits of a control IC section 2308, a system 2300 can further include one or more supplemental storage circuits 2308-1 accessible by a control IC section 2308. Preferably, supplemental storage circuits 2308-1 can be a single nonvolatile memory IC, even more preferably an EEPROM IC.

A transmitting section 2310 can receive characteristic values from control IC section 2308 and output such values on a communication path 2330 to a location remote from system 2300. In the particular example shown, transmitting section 2310 can be a wireless universal serial bus (USB) IC that sends a wireless signal according to a conventional wireless USB protocol. Such an arrangement can eliminate the need to physically wire a monitoring/communication path between a capacitance sensor and a remote location at which a monitoring system resides. However, as shown below, other embodiments can provide an output suitable for transmission over a physical wiring.

While a system can transmit a characteristic value as data, in addition or alternatively, such values can be provided by visual indications. In the particular example of FIG. 23, system 2300 can include a value display 2324 and/or and a status display 2326, and/or an audio 2327 output. A value display 2324 can display a characteristic value generated by system 2300. A value display 2324 can preferably be an alphanumeric liquid crystal display (LCD), but may take alternate forms, such as an LED alphanumeric display, as but one example. A status display 2326 can be provided to indicate a status for system 2300. For example, a status display 2326 can indicate when a material characteristic is out of a range (i.e., level too low, level too high, container tipped, sense material changed, etc.).

Figure 24:
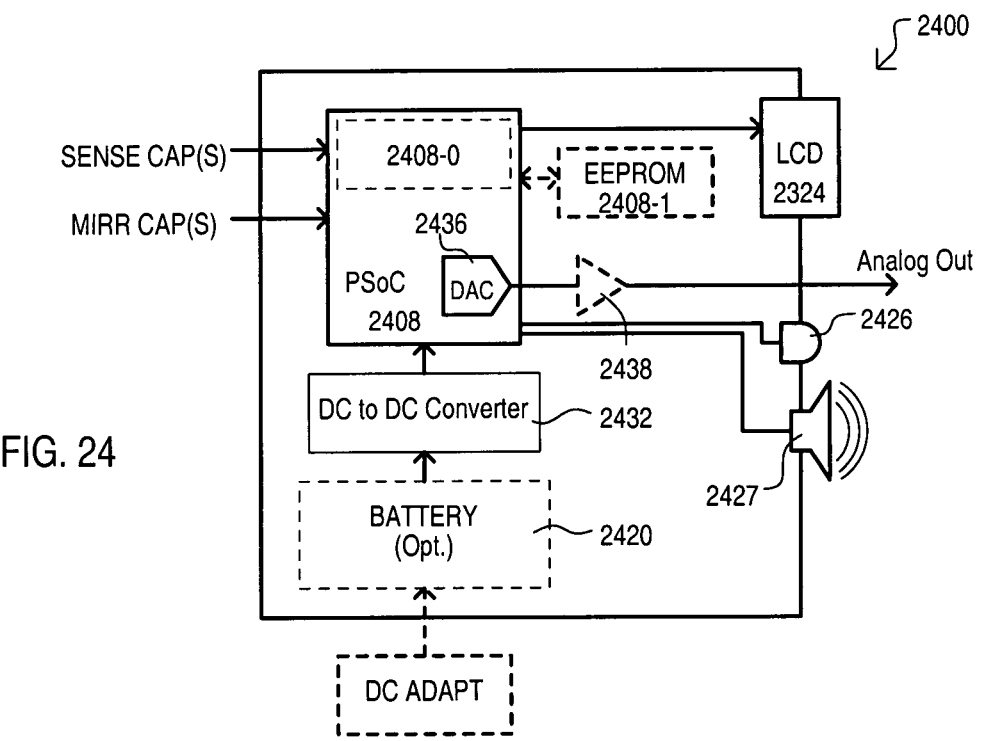

Referring now to FIG. 24, a capacitance sensing system according to another embodiment is shown in a block diagram and designated by the general reference character 2400. A system 2400 includes some of the same general sections as the embodiment of FIG. 23, accordingly, like sections are referred to by the same reference character but with the first digit being a "24" instead of a "23".

A system 2400 can differ from that of FIG. 23 in that it can provide an analog output signal. More particularly, system 2400 can include a digital-to-analog converter (DAC) 2436 that can convert a material characteristic value into an analog signal for output to a remote location. Preferably, DAC 2436 can be formed from a portion of control IC section 2408. Optionally, a system 2400 can include an amplifier circuit 2438 for amplifying the analog output signal from control IC section 2408 into a transmitted signal. Such an analog output signal can be an industry standard signal suitable for use with control systems based on analog signals.

Referring now to FIG. 25, a capacitance sensing system according to another embodiment is shown in a block diagram and designated by the general reference character 2500. A system 2500 includes some of the same general sections as the embodiment of FIG. 23, accordingly, like sections are referred to by the same reference character but with the first digit being a "25" instead of a "23".

A system 2500 can differ from that of FIG. 23 in that it can include a network interface 2540. A network interface 2540 can transmit and receive data in packet format over a network connection 2542. A network connection 2542 can be wired or wireless connection. A network connection can connect to a local area network (LAN), wide are network (WAN), or the Internet, for example.

In this way, a system 2500 can be a compact and easily implemented device that is suitable for monitoring over a network.

While embodiments of the present invention can include single capacitance sense systems, other embodiments can include multiple such systems. Examples of such embodiments will now be described.

Referring now to FIG. 26, a system is shown in a diagram and designated by the general reference character 2600. A system 2600 can include one or more capacitance sensing systems 2602 and a monitoring device 2604. In the example of FIG. 26, sensing systems 2602 can each include a wireless transmitter that transmits data to a monitoring device 2604.

In the arrangement of FIG. 26, each sensing system 2602 can transmit data over a separate wireless channel. Such data can include material characteristic data, as noted in the embodiments above. In one very particular example, data can be transmitted via wireless USB protocol.

A monitoring device 2604 can include a wireless receiver capable of receiving data via a wireless link. In the event a system 2600 includes more than one sensing system, a monitoring system 2600 can include a wireless receiver capable of distinguishing between the multiple channels. It is understood that a monitoring device 2604 may be but one portion of a larger process control system. Further, in other embodiments, a system may include multiple monitoring devices that each monitor data for one, or a select group of sensing systems.

Referring now to FIG. 27, another system is shown in a diagram and designated by the general reference character 2700. A system 2700 can include some of the same general sections as the embodiment of FIG. 26, accordingly, like sections are referred to by the same reference character but with the first digit being an "27" instead of a "26".

System 2700 can differ from that of FIG. 26 in that each sense system 2702 can include a wired transmitter circuit. Thus, data from the sense systems 2702 can be transmitted via wired channels. In addition, readings can be received via analog inputs of an analog monitoring system 2712.

Figure 28:
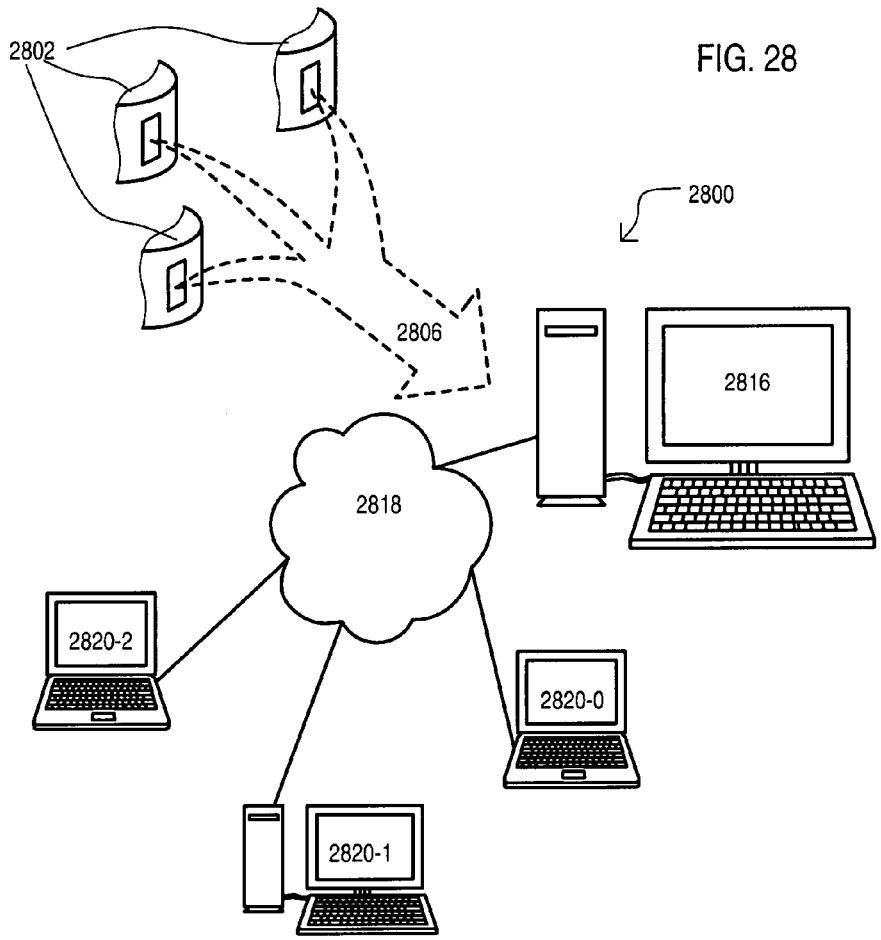

Referring now to FIG. 28, yet another system is shown in a diagram and designated by the general reference character 2800. A system 2800 can have sense systems 2802 that can transmit data over connections 2806 to a monitoring device 2816. Connections 2806 can be wireless connections, in which case sense systems 2802-0 can include wireless transmitters, or can be wired connections, in which case sense systems 2802 can include wired transmitters, or some combination thereof.

A monitoring device 2816 can be network server that can receive and store data received from a sense system. Monitoring device 2816 can be connected to a network 2818, and thus enable access to such sense system data via one or more client devices (2820-0, 2820-1, 2820-2) via data packet communication protocols. A network 2818 can include a LAN, WAN or the Internet, as but a few examples, and can be connectionless or connection oriented.

While the invention may have numerous applications in wide range of industries, one very particular application is shown in an embodiment in FIGS. 29(a) and (b).

Figure 29:
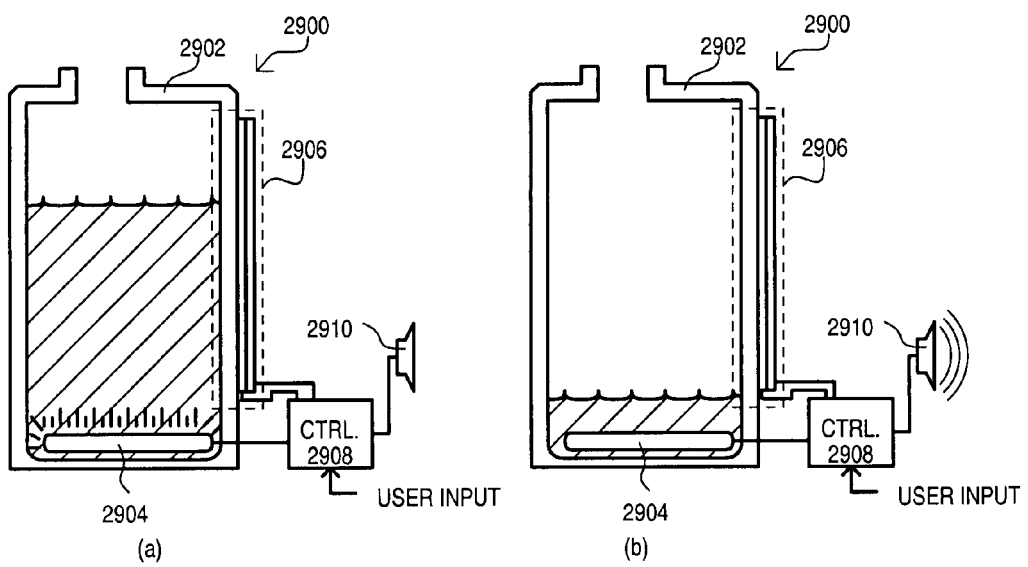
FIG. 29 is a diagram showing a humidifier system according to an embodiment of the invention.

Referring now to FIG. 29, a humidifier system according to an embodiment is shown in a diagram and designated by the general reference character 2900. A system 2900 can include a reservoir 2902, a heating element 2904, a sensor assembly 2906, a controller 2908 and an alarm 2910. A reservoir 2902 can be designed to receive and contain water.

A heating element 2904 can be situated at a bottom of reservoir 2902, and can be placed into an active or inactive state according to controller 2908. In the active state, current can flow through heating element 2904 generates heat in order to evaporate water within reservoir 2902. In the arrangement shown, a heating element 2904 can be damaged or its operating life shortened if it is exposed to air while activated (i.e., while it is not covered by water).

A sensor assembly 2906 can include capacitance sensing structures like those described above, or equivalents, including one or more sense plates having a sense side facing reservoir 2902, and one or more corresponding mirror plates separated from the reservoir 2902 by such sense plate.

A controller 2908 can acquire capacitance values from detector assembly 2906, and in response to such values, activate or deactivate heating element 2904, and activate or deactivate alarm 2910. Alarm 2910 can be a visual and/or audio alarm, or can be a signal, as but a few examples.

As shown in FIG. 29(a), in operation, a reservoir 2902 can be filled with water. In response to user inputs, a controller 2908 can start a humidifying operation by activating heating element 2904. Controller 2908 can monitor water levels using capacitance sensing techniques noted above. As shown in FIG. 29(b), when a water level drop to low level, but at a level sufficient to keep heating element 2904 submerged, controller 2908 can deactivate heating element 2904 and activate alarm 2910.

In one very particular arrangement of a system like that of FIG. 29, a capacitance value presented by a mirror plate can represent a limit value indicating a reservoir has reached a low limit. A controller 2908 can compare a sense plate capacitance value to that of a mirror plate. If a sense capacitance value is at or near a mirror plate value, a heating element 2904 can be deactivated and/or alarm 2910 can be activated.

As noted above, in the various embodiments, a material can be in solid form, liquid or gaseous form. In the case of gases and liquids, such material may be essentially motionless, or may be flowing through a container, such as a pipe or tube. A material characteristic value output from the various systems can be used to trigger other events in a system.

The above embodiments have described capacitance values that can be derived from a sense plate and/or mirror plate. Such values can be counts, as indicated above, utilizing relaxation oscillator and/or sigma-delta modulation techniques. "Raw" counts can be utilized to generate material characteristic values (e.g., level of material, orientation of container or material, concentration of material). However, such values can also be modified from such raw counts. As a few of the many examples, capacitance values can be generated by scaling raw counts (RawCount*K), rounding raw counts (e.g., dropping bits of lesser significance), averaging raw counts, taking a mean from a set of raw counts, or using one or more maximum or minimum raw count values.

While sensing operations can take various examples, a few generation examples will be described below. Below shows a pseudocode example of sensing operation with hysteresis:
Basic Alarm (with Hysteresis)

```
While Alarm = 0
    Generate SenseCap, MirrorCap
    If SenseCap > MirrorCap
        Continue
    Else
        Alarm = 1
While Alarm = 1
    Generate SenseCap, MirrorCap
    If SenseCap < MirrorCap + Buffer
        Continue
    Else
        Alarm = 0
```

"Alarm" can be an alarm indication. "SenseCap" can be a capacitance value for a sense plate. "MirrorCap" can be a capacitance value for a mirror plate.

In this way, a method can utilize a mirror capacitance value as a level limit indicator.

While embodiments can utilize mirror capacitance values to generate limits, other embodiments can utilize such values to generate a level value. A general level sensing operation is shown in pseudocode. Such an operation can rely on a single sense value (i.e., it does not use multiple discrete sense plate):
Basic Level Sense—
   Generate SenseCap, MirrorCap
   Level=f{SenseCap, MirrorCap}
   Output Level The above utilizes a predetermined function "f{SenseCap, MirrorCap}" for calculating a level. Such a function can vary according to the geometry of the sensing plates, relation of plate size to sensed volume, and permittivity of material. A few possible examples include functions based on linear relationships (e.g., F=(SenseCap−MirrorCap)*K) or non-linear relationships, such as exponential functions (F=K e ^(SenseCap−MirrorCap), and logarithmic functions F=K ln(SenseCap−MirrorCap), to name but three very general examples.

While one embodiment has described the sensing of water levels, other embodiments can be used to determine the characteristics of other liquids, including but not limited to hydrocarbon based liquids.

Embodiments of the present invention are well suited to performing various other steps or variations of the steps recited herein, and in a sequence other than that depicted and/or described herein.

For purposes of clarity, many of the details of the various embodiments and the methods of designing and manufacturing the same that are widely known and are not relevant to the present invention have been omitted from the following description.

It should be appreciated that reference throughout this specification to "one embodiment" or "an embodiment" means that a particular feature, structure or characteristic described in connection with the embodiment is included in at least one embodiment of the present invention. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the invention.

Similarly, it should be appreciated that in the foregoing description of exemplary embodiments of the invention, various features of the invention are sometimes grouped together in a single embodiment, figure, or description thereof for the purpose of streamlining the disclosure aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

It is also understood that the embodiments of the invention may be practiced in the absence of an element and/or step not specifically disclosed. That is, an inventive feature of the invention can be elimination of an element.

Accordingly, while the various aspects of the particular embodiments set forth herein have been described in detail, the present invention could be subject to various changes, substitutions, and alterations without departing from the spirit and scope of the invention.

What is claimed is:

1. A system for sensing characteristics of a volume, comprising:
   at least one mirror input configured to connect to at least a first mirror plate, the first mirror plate being physically isolated from a first monitor space for containing a material;
   at least one sense input configured to connect to at least a first sense plate that is interposed between the at least first mirror plate and the first monitored space and that has one surface that faces the first monitored space; and
   a capacitance sense section that generates a first sense value based on a capacitance at the at least one sense input, and a mirror value based on the capacitance at the at least one mirror input.

2. The system of claim 1, wherein:
   the first monitored space is enclosed by a container having at least one inner container surface exposed to the first monitored space and an outer container surface not exposed to the first monitored space; and
   the at least first sense plate has a first surface attached to the outer container surface.

3. The system of claim 1, wherein:
   the first monitored space is enclosed by a container having at least one inner container surface exposed to the first monitored space and an outer container surface not exposed to the first monitored space; and
   the at least first sense plate has a first surface that is physically exposed to the first monitored space.

4. The system of claim 1, wherein:
   the first monitored space is enclosed by a container; and
   the material is selected from the group consisting of a liquid, a gas, and solid in particulate form.

5. The system of claim 1, wherein:
   the at least first mirror plate is formed from the same material as the at least first sense plate.

6. The system of claim 5, wherein:
   the at least first mirror plate has the same physical dimensions as the at least first sense plate.

7. The system of claim 1, wherein:
   the space occupied by the material can vary in at least a first direction with respect to a surface of the container; and
   the at least first mirror plate comprises a plurality of mirror plates separated from one another in the first direction; and
   the at least first sense plate comprises a plurality of sense plates, each sense plate being interposed between a corresponding one of the mirror plates and the first monitored space.

8. The system of claim 1, wherein:
   a portion of the space occupied by the material can vary with respect to at least a first direction;
   the at least first mirror plate comprises a plurality of mirror plates separated from one another in a second direction essentially perpendicular to the first direction; and
   the at least first sense plate comprises a plurality of sense pates, each sense plate being interposed between a corresponding one of the mirror plates and the first monitored space.

9. The system of claim 1, further including:
   the at least a first mirror plate is physically isolated from a second monitored space;
   a second sense input configured to connect to at least a second sense plate that is interposed between the at least mirror plate and the second monitored space and that has one surface that faces the second monitored space; and
   the capacitance sense section generates a second sense value based on a capacitance at the second sense input.

10. The system of claim 1, wherein:
    the at least first mirror plate has a reference surface that faces a second monitored space different from the first monitored space, the reference surface being a side of the mirror plate opposite to a side that faces the at least first sense plate.

11. The system of claim 1, wherein:
    the at least first sense plate has different physical dimensions than the at least first mirror plate.

12. The system of claim 1, wherein:
    the space is enclosed by a container having a wall;
    the at least first sense plate is fixed to the wall; and
    the at least first mirror plate is removable and can be removed from a position adjacent to the at least first sense plate.

13. The system of claim 1, wherein:
    the capacitance sense section includes ain input multiplexer for selectively connecting the at least one sense input and at least one mirror input to a common sense node.

14. The system of claim 13, wherein:
    the capacitance sense section further includes
    at least one comparator having a first input coupled to the sense node and a second input coupled to a threshold voltage source, and
    a switch circuit having a controllable impedance path coupled to the sense node operable in response to an output of the at least one comparator.

15. The electronic system of claim 13, wherein:
the capacitance sense section further includes a counter having an input coupled to the output of the comparator that generates a value that varies according to a sensed capacitance at the sense node.

16. A system for detecting the characteristics of at least one material occupying at volume, comprising:
at least one sense plate having a first sense side that faces a first volume and an opposing second sense side;
at least one mirror plate that is isolated from the first volume having a first mirror side that faces the first sense side; and
a controller section that generates a characteristic value based on a capacitance of the at least one sense plate and the at least one mirror plate measured independently of one another.

17. The system of claim 16, wherein:
the controller section includes a capacitance sense section comprising at least one relaxation oscillator circuit having an oscillation rate that varies according to at least the capacitance of the at least one the sense plate.

18. The system of claim 17, wherein:
the relaxation oscillator circuit oscillation rate varies according to at least the capacitance at a sense node, and
a switch circuit for selectively connecting the sense plate or the mirror plate to the sense node.

19. The system of claim 16, wherein:
the capacitance sense section comprises a delta sigma modulation circuit that includes a comparator that switches output states according to at least the capacitance of the at least one the sense plate.

20. The electronic system of claim 16, wherein
the characteristic value varies according to the amount of monitored space occupied by the material.

21. The system of claim 16, further including:
the at least one mirror plate has a second mirror side that faces a second volume; and
the characteristic value corresponds to a difference in capacitance arising from a first material opposite the first sense side and a second material opposite the second mirror side.

22. The system of claim 16, wherein:
the characteristic value activates an indicator selected from the group consisting of: an illumination source, a character display, an audio alarm.

23. The system of claim 16, wherein:
the controller section further includes a wireless transmitter that transmits at least the material value over a wireless connection.

24. The system of claim 16, wherein:
the controller section further includes a network interface that transmits at least the material value in packet form over a data communication network.

25. The system of claim 16, further including:
a reservoir having a bottom and at least a surrounding side surface that defines at least a portion of the first volume;
a heating element disposed at the bottom of the reservoir;
the at least one sense plate being attached to the side surface of the reservoir; and
the characteristic value being coupled to the heating element.

26. A method of sensing the characteristic of a material occupying a volume:
measuring a mirror capacitance of a mirror plate positioned adjacent to, but outside of a monitored volume;
measuring a sense capacitance of a sense plate positioned between the mirror plate and the monitored volume; and
generating a characteristic value based on the mirror capacitance and sense capacitance.

27. The method of claim 26, wherein:
the step of measuring the mirror capacitance includes generating a mirror count corresponding to an amount of time needed to charge and discharge the mirror plate between two predetermined potentials; and
the step of measuring the sense capacitance includes generating a sense count corresponding to an amount of time needed to charge and discharge the sense plate between the two predetermined potentials.

28. The method of claim 27, wherein:
generating the characteristic value includes activating a limit indication when the sense count varies from the mirror count by a predetermined amount.

29. The method of claim 26, wherein:
the step of measuring the mirror capacitance includes
coupling the mirror plate to the first potential node,
coupling the mirror plate to a first input of a comparator that has a second input coupled to a reference voltage node,
coupling the input of the comparator to a second node based on the output of the comparator, and
the mirror count corresponds to the number of times the comparator output is high versus the number of times the comparator output is low.

30. The method of claim 26, wherein:
measuring the mirror capacitance includes periodically measuring the mirror capacitance at a first rate;
measuring the sense capacitance includes periodically measuring the sense capacitance at the first rate.

31. The method of claim 26, wherein:
measuring the mirror capacitance includes periodically measuring the mirror capacitance at a first rate;
measuring the sense capacitance includes periodically measuring the sense capacitance at a second rate different from the first rate.

* * * * *